US00PP09366P

United States Patent [19]

Hope

[11] Patent Number: Plant 9,366

[45] Date of Patent: Nov. 7, 1995

[54] KALANCHOE PLANT NAMED 'PICO TICO BRIGHT PINK'

[75] Inventor: Claude Hope, Cartago, Costa Rica

[73] Assignee: Ball Seed Co., West Chicago, Ill.

[21] Appl. No.: 380,012

[22] Filed: Jan. 27, 1995

[51] Int. Cl.[6] ..... A01H 5/00

[52] U.S. Cl. ..... Plt./87.15

[58] Field of Search ..... Plt./87.15

*Primary Examiner*—James R. Feyrer

*Attorney, Agent, or Firm*—C. A. Whealy

[57] ABSTRACT

A distinct cultivar of Kalanchoe plant named Pico Tico Bright Pink, characterized by its very compact plant growth habit; freely branching habit; proportional leaf size; flowers that are borne just above the foliage; peduncles that do not stretch during flowering or during postproduction; bright pink flower color; and excellent keeping quality.

1 Drawing Sheet

The present invention relates to a new and distinctive cultivar of Kalanchoe plant, botanically known as *Kalanchoe blossfeldiana,* and hereinafter referred to by the cultivar name Pico Tico Bright Pink.

The new cultivar is a product of a planned breeding program conducted by the inventor in Cartago, Costa Rica.

The new cultivar originated from a cross made by the inventor of the proprietary selection KLV 80-47-P1 as the male or pollen parent with the proprietary selection KCR 249-2-1 as the female or seed parent.

The cultivar Pico Tico Bright Pink was discovered and selected by the inventor as a flowering plant within the progeny of the stated cross in a controlled environment in Cartago, Costa Rica. Asexual reproduction of the new cultivar by terminal cuttings taken at Cartago, Costa Rica, and subsequently at West Chicago, Ill., has shown that the unique features of this new Kalanchoe are stabilized and reproduced true to type in successive generations of asexual reproduction.

The cultivar Pico Tico Bright Pink has not been observed under all possible environmental conditions. The phenotype may vary somewhat with variations in environment such as temperature, daylength and light intensity, without, however, any variance in genotype. The following observations, measurements and comparisons describe plants grown in West Chicago, Ill., under commercial practice in a glass-covered greenhouse.

The following traits have been repeatedly observed and are determined to be the unique characteristics of Pico Tico Bright Pink. These characteristics in combination distinguish Pico Tico Bright Pink as a new and distinct cultivar:

1. Very compact plant growth habit. Plants do not require plant growth retardants and can be produced in 8-cm or smaller containers.
2. Plants are freely branching and do not require pinching.
3. Leaf size is proportional to plant size.
4. Peduncles do not stretch during flowering or during postproduction.
5. Petals are bright pink in color.
6. Plants have excellent keeping quality. Flowers maintain good substance and foliage maintains good color for six weeks under interior conditions.
7. Flowers are borne just above the foliage giving plants a mounded appearance.

The new Kalanchoe differs from its parents in the color of the petals. The petal color of the male parent, KLV 80-47-P1, is carmine red; and the petal color of the female parent, selection KCR 249-2-1, is light yellow or cream in contrast to the medium pink color of Pico Tico Bright Pink petals.

Pico Tico Bright Pink is most similar to the Kalanchoe cultivar Pico Tico Cherry in its compact growth habit and suitability for small containers. However Pico Tico Bright Pink differs from Pico Tico Cherry in the following characteristics:

1. Plants of Pico Tico Bright Pink have medium pink flowers compared to the cherry red flowers of Pico Tico Cherry.
2. Plants of Pico Tico Bright Pink have fewer flowers per cyme than plants of Pico Tico Cherry.

The accompanying colored photograph illustrates the overall appearance of the new cultivar, showing the colors as true as it is reasonably possible to obtain in colored reproductions of this type. The photograph comprises a side perspective view of a typical potted plant of Pico Tico Bright Pink.

In the following description, color references are made to The Royal Horticultural Society Colour Chart except where general terms of ordinary dictionary significance are used. Measurements and numerical values represent averages for eight typical plants.

Botanical classification: *Kalanchoe blossfeldiana* cultivar Pico Tico Bright Pink.

Parentage:

*Male.*—Proprietary selection KLV 80-47-P1.

*Female.*—Proprietary selection KCR 249-2-1.

Propagation:

A. *Type cutting.*—Terminal tip cuttings.

B. *Time to initiate roots.*—7 days at 25° C. soil temperature.

C. *Rooting habit.*—Fine, fibrous, and well-branched.

Plant description:

A. *Form.*—Upright and moderately compact.

B. *Habit of growth.*—Freely branching.

C. *Plant height at flowering.*—12 cm.

D. *Foliage description.*—1. Size: a. Length: 8 cm. b. Width: 6 cm. 2. Shape: Ovate. 3. Texture: Succulent. 4. Margin: Crenate. 5. Color: a. Young foliage top side: 147A. b. Young foliage under side: 147B. c. Mature foliage top side: 147A. d. Mature foliage under side: 147B. e. Leaf margin: 59A.

E. *Stem description.*—1. Main stem diameter: 0.7 cm. 2. Color: 147B.

Flower description:

A. *Flower type and habit.*—Freely flowering, flowers arranged in panicles, cymose.

B. *Natural flowering season.*—Autumn/winter in Northern Hemisphere. Flower imitation and development can be induced under short day/long night conditions.

C. *Flowers borne.*—Just above foliage, arising from leaf axils.

D. *Quantity of flowers.*—35 on lateral cymes, 35 on main cyme.

E. *Petals.*—1. Shape: Elliptic. 2. Base: Linear. 3. Tip: Acute. 4. Size: a. Length: 1.4 cm. b. Width: 0.8 cm. 5. Color: a. When opening: 61C. b. Mature, top side: 61C. c. Mature, under side: 63B. d. Fading to: 63B/63C. e. Peduncle: 147B.

F. *Reproductive organs.*—1. Stamens: a. Stamen number: 8. b. Anther color: 143B. c. Pollen color: 5B. 2. Pistils: a. Stigma color: 3C. b. Style color: 143B. c. Ovary number: 4. d. Ovary size: (1) Length: 4 mm. (2) Width: 1 mm. e. Ovary color: 143B.

Disease resistance: No fungal, bacterial nor viral problems observed.

Seed production: Seed production has not been observed.

I claim:

1. A new and distinct cultivar of Kalanchoe plant named Pico Tico Bright Pink, as illustrated and described.

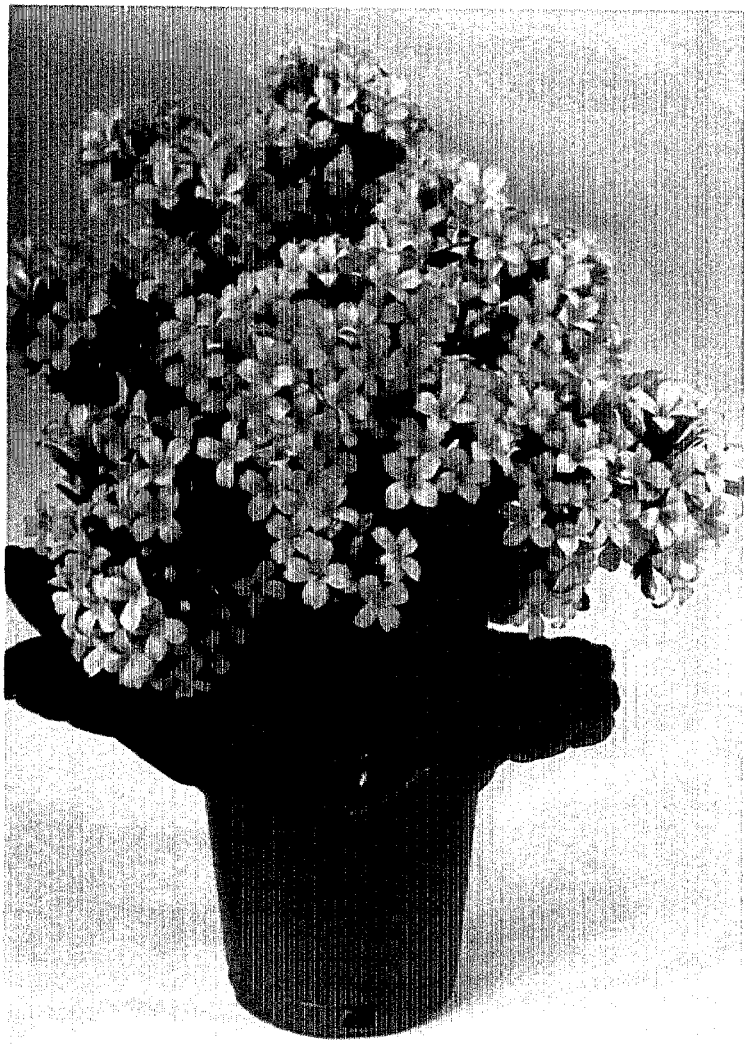

* * * * *